(12) United States Patent
Sun et al.

(10) Patent No.: US 9,965,656 B2
(45) Date of Patent: *May 8, 2018

(54) METHODS AND APPARATUS FOR COMPUTER-AIDED TISSUE ENGINEERING FOR MODELING, DESIGN AND FREEFORM FABRICATION OF TISSUE SCAFFOLDS, CONSTRUCTS, AND DEVICES

(71) Applicant: Drexel University, Philadelphia, PA (US)

(72) Inventors: Wei Sun, Cherry Hill, NJ (US); Jae Hyun Nam, Broomall, PA (US); Andrew Leete Darling, Syracuse, NY (US); Saif Khalil, King of Prussia, PA (US)

(73) Assignee: Drexel University, Philadelphia, PA (US)

( * ) Notice: Subject to any disclaimer, the term of this patent is extended or adjusted under 35 U.S.C. 154(b) by 278 days.

This patent is subject to a terminal disclaimer.

(21) Appl. No.: 14/924,801

(22) Filed: Oct. 28, 2015

(65) Prior Publication Data

US 2016/0046078 A1    Feb. 18, 2016

Related U.S. Application Data

(63) Continuation of application No. 14/153,764, filed on Jan. 13, 2014, now abandoned, which is a
(Continued)

(51) Int. Cl.
*G06G 7/48* (2006.01)
*B29C 67/00* (2017.01)
(Continued)

(52) U.S. Cl.
CPC ............... *G06G 7/48* (2013.01); *A61K 47/36* (2013.01); *B29C 67/0059* (2013.01);
(Continued)

(58) Field of Classification Search
CPC ....................................................... G06G 7/48
(Continued)

(56) References Cited

U.S. PATENT DOCUMENTS

| 4,575,330 A | 3/1986 | Hull |
| 4,584,590 A | 4/1986 | Fischbeck et al. |

(Continued)

FOREIGN PATENT DOCUMENTS

| EP | 1002570 A1 | 5/2000 |
| WO | WO89/08021 A1 | 9/1989 |

(Continued)

OTHER PUBLICATIONS

Ang., T. H., et al., 2002, "Fabrication of 3D chitosan-hydroxyapatite scaffolds using a robotic dispending system", Materialsl Science Engineering, C 20, 35-42.
(Continued)

*Primary Examiner* — Hugh Jones
(74) *Attorney, Agent, or Firm* — Saul Ewing Arnstein & Lehr LLP; Kathryn Doyle; Brian R. Landry (57) ABSTRACT

One aspect of the invention provides a method for multi-nozzle biopolymer deposition of heterogeneous materials to create or modify a composite biopolymer multi-part three-dimensional assembly having at least one biomimetic and at least one non-biomimetic feature. The method includes: (a) utilizing a CAD environment to design and/or modify a composite multi-part assembly, thereby producing a CAD design; (b) converting the CAD design into a three-dimensional heterogeneous material and multi-part assembly model in a format suitable for three-dimensional, multi-nozzle printing, wherein the design comprises at least one biomimetic feature and at least one non-biomimetic feature; and (c) printing the composite assembly by simultaneously depositing the heterogeneous materials using multiple, dif-
(Continued)

ferent, specialized nozzles, wherein the simultaneous depositing includes direct deposition of cells.

10 Claims, 4 Drawing Sheets

Related U.S. Application Data continuation of application No. 10/540,968, filed as application No. PCT/US2004/015316 on May 14, 2004, now Pat. No. 8,639,484.

(60) Provisional application No. 60/520,272, filed on Nov. 14, 2003.

(51) Int. Cl.

| | | |
|---|---|---|
| G06F 17/50 | (2006.01) | |
| A61K 47/36 | (2006.01) | |
| G05B 19/042 | (2006.01) | |
| C12N 5/071 | (2010.01) | |
| G05B 19/4099 | (2006.01) | |
| C12N 5/00 | (2006.01) | |
| B29C 41/52 | (2006.01) | |
| B33Y 50/02 | (2015.01) | |

(52) U.S. Cl.
CPC ........ *B29C 67/0088* (2013.01); *C12N 5/0062* (2013.01); *C12N 5/0691* (2013.01); *G05B 19/042* (2013.01); *G05B 19/4099* (2013.01); *G06F 17/50* (2013.01); *B29C 41/52* (2013.01); *B33Y 50/02* (2014.12); *C12N 2513/00* (2013.01); *C12N 2533/74* (2013.01); *G05B 2219/35134* (2013.01); *G05B 2219/49007* (2013.01)

(58) Field of Classification Search
USPC .......................................................... 703/10
See application file for complete search history.

(56) References Cited

U.S. PATENT DOCUMENTS

| | | |
|---|---|---|
| 5,136,515 A | 8/1992 | Helinski |
| 5,204,055 A | 4/1993 | Sachs et al. |
| 5,402,351 A | 3/1995 | Batchelder et al. |
| 5,649,277 A | 7/1997 | Greul et al. |
| 6,027,744 A | 2/2000 | Vacanti et al. |
| 6,139,574 A | 10/2000 | Vacanti et al. |
| 6,143,293 A | 11/2000 | Weiss et al. |
| 6,171,610 B1 | 1/2001 | Vacanti et al. |
| 6,176,874 B1 | 1/2001 | Vacanti et al. |
| 6,261,493 B1 | 7/2001 | Gaylo et al. |
| 6,309,891 B1 | 10/2001 | Shalon et al. |
| 6,333,194 B1 | 12/2001 | Levy et al. |
| 6,405,095 B1 | 6/2002 | Jang et al. |
| 6,454,811 B1 | 9/2002 | Sherwood et al. |
| 6,547,994 B1 | 4/2003 | Monkhouse et al. |
| 6,623,687 B1 | 9/2003 | Gervasi et al. |
| 6,730,252 B1 | 5/2004 | Teoh et al. |
| 6,772,026 B2 | 8/2004 | Bradbury et al. |
| 7,051,654 B2 | 5/2006 | Boland et al. |
| 8,639,484 B2 | 1/2014 | Sun et al. |
| 2001/0008317 A1 | 7/2001 | Gaylo et al. |
| 2004/0254668 A1 | 12/2004 | Jang et al. |

FOREIGN PATENT DOCUMENTS

| | | |
|---|---|---|
| WO | WO00/29202 A1 | 5/2000 |
| WO | WO02/064353 A1 | 8/2002 |

OTHER PUBLICATIONS

Calvert, P., et al., 1998, "Solid freeform fabrication of organic-inorganic hybrid materials", Materials Science and Engineering, 6, 167-174.
Cho, W., et al., 2001, "Solid Freeform Fabrication with Local Composition Control", Rapid Protytyping, 7(2), 1-8.
Griffith L. G., et al., 2006, "In Vitro Organogenesis of Liver Tissue", Annals New York Academy of Sciences, 831(1), 382-397.
Hu, X., et al., 2000, "Computer-Aided Composite Unit Cell Design and Modeling", In Proc. of American Society of Composite, 15, 609-620.
Landers, R., et al., 2001, "Desktop Manufacturing and Biofunctional Processing" Kunststoffe/plast Europe, 91(12), 21-23.
Landers, R., et al., 2002, "Rapid prototyping of scaffolds derived from thermoreversible hydrogels and tailored for applications in tissue engineering", Biomaterials, 23, 4437-4447.
Landers, R., et al., 2000, "Desktop manufacturing of complex objects, prototypes and biomedical scaffolds by means of computer-assisted design combined with computer-guided 3D plotting of polymers and reactive oligomers", Macromol. Mater. Eng. 282, 17-21.
Lau, W., et al., 2002, "XML Representation and Process Algorithm for Layered Manufacturing of Heterogeneous Objects" In Proc. of Thirteenth Solid Freeform Fabrication Symposium, Austin, TX, 255-266.
Li, R. H., 1998, "Materials for immunoisolated cell transplantation", Advanced Drug Delivery Reviews, 33, 87-109.
Lin, F., et al., 1999, "A Mathematical Description of Layered Manufacturing Fabrication", In Proc. of the 10th Solid Freeform Fabrication Symposium, Austin, TX, 139-146.
Minorov, V., et al., 2003, "Organ printing: computer-aided jet-based 3D tissue engineering", Trends in Biotechnology, 21, 157-161.
Reischmann, M., et al., 2002, "Prototype implementation of an assembly system for tissue engineered constructs", Electrotechnik and Informationstechnick, 248-252.
Starly, B., et al., 2002, "'Biomimetic' Model for Heterogeneous Bone Scaffold", Biomedical Engineering: Recent Developments, 305-306.
Sun, W., et al., 1997, "Knowledge-enriched CAD Modeling for Solid Freeform Realization of Heterogeneous Material Structures", In Proc. of the Seventh International Conference on Rapid Prototyping, San Francisco, CA, 79-87.
Sun, W., 2000, "Multi-Volume CAD Modeling for Heterogeneous Object Design and Fabrication", J. Comput. Sci. & Technol., 15(1), 27-36.
Sun, W., et al., 2002, "Reasoning Boolean operation based modeling for heterogeneous objects", Computer-Aided Design, 34, 481-488.
Sun, W., et al., 2002, "Recent development on computer aided tissue engineering—a review", Computer Methods and Programs in Biomedicine, 67, 85-103.
Vozzi, G., et al., 2002, "Microfabricated PLGA scaffolds: a comparative study for application to tissue engineering", Materials Science and Engineering, 20, 43-47.
Vozzi, G., et al., 2003, "Fabrication of PLGA scaffolds using soft lithography and microsyringe deposition", Biomaterials, 24, 2533-2540.
Weiss, L. E., et al., 1997, "Shape Deposition Manufacturing of Heterogeneous Structures", Journal of Manufacturing Systems, 16(4), 239-248.
Xiong Z., et al., 2002, "Fabrication of porous scaffolds for bone tissue engineering via low-temperature deposition", Scripta Meterialia, 46, 771-776.
Yan, Y., et al., 2003, "Layered manufacturing of tissue engineering scaffolds via multi-nozzle deposition", Materials Letters, 57(18), 2623-2628.
Zein, I., et al., 2002, "Fused deposition modeling of novel scaffold architectures for tissue engineering applications", Biomaterials, 23, 1169-1185.
Zhao, X., et al., 2001, "Ceramic Freeforming Using an Advanced Multinozzle Ink-Jet Printer", Journal of Materials Synthesis and Processing, 9(6), 319-327.

(56) References Cited

OTHER PUBLICATIONS

Wang, F., et al., 2004, "Precision extruding deposition and characterization of cellular poly-ϵ-caprolactone tissue scaffolds", Rapid Prototyping Journal, 10, 42-49.

Chang, R., et al., Drexel University Biofabrication Lab, Publication List, http//www.mem.drexel.edu/BFLab/publications/index.html, 17 pages, downloaded Jan. 6, 2011.

Cooley, P., et al., "Applications of Ink-Jet Printing Technology to BioMEMS and Microfluidic Systems", in Proc. of SPIE Conference on Microfluidics and BioMEMS, pp. 1-12, Oct. 2001.

O'Costa, D. J., et al., "Three-Dimensional Printing of Layered Machinable Ductile Carbide", In Proc. Engineering Symposium, Texas, 2 pages, Aug. 7-9, 2000.

Darling, et al., "Biomodeling Assisted Three Dimensional Organ Printing", Biomedical Engineering: Recent Developments: Editor, J. Vossoughi, 2002 Medical and Engineering Publishers, Inc., pp. 237-238, Sep. 2002.

Hu, et al., "Reasoning Boolean Operation for Modeling, Simulation and Fabrication of Heterogeneous Objects", In Proc. of Eleventh Solid Freeform Fabrication Symposium, University of Texas, Austin, TX, 11 pages, Aug. 7-9, 2000.

Jiang, "Anatomical Modeling and Rapid Prototyping Assisted Surgical Reconstruction", In Proc. of the Eleventh Solid Freeform Fabrication Symposium, University of Texas, Austin, TX, pp. 1-9, Aug. 7-9, 2000.

Lee, "Design and Synthesis of Biocompatible Ceramic/Polymer Composites Via Stereolithography", A Dissertation Presented to the Faculty of Princeton University in Candidacy for the Degree of Doctor of Philosophy, 254 pages, Nov. 2002.

Lewandrowski, et al., "Tissue Engineering and Biodegradable Equivalents", Marcel Dekker, Inc., 17 pages, 2002 (downloaded Jun. 13, 2007).

Starly, et al., "Layered Composite Model for Design and Fabrication of Bone Replacement", Proc. of 13th Solid Freeform Fabrication Symposium, Austin, TX, vol. 8, pp. 24-34, Aug. 2002.

METHODS AND APPARATUS FOR COMPUTER-AIDED TISSUE ENGINEERING FOR MODELING, DESIGN AND FREEFORM FABRICATION OF TISSUE SCAFFOLDS, CONSTRUCTS, AND DEVICES

This patent application is a continuation of U.S. Ser. No. 14/153,764, filed Jan. 13, 2014, which is a continuation of U.S. patent application Ser. No. 10/540,968, filed Jun. 29, 2005, and issued as U.S. Pat. No. 8,639,484 on Jan. 28, 2014, which is a national phase application of International Application No. PCT/US2004/015315, filed May 14, 2004 and which claims priority to U.S. Provisional Patent Application Ser. No. 60/520,272, filed Nov. 14, 2003, all of which are herein incorporated by reference in their entirety.

FIELD OF THE INVENTION

The present invention provides methods and apparatus for manufacturing complex devices for use in areas including, but not limited to, tissue engineering, organ/cell printing, tissue scaffolds, tissue cultures, biochips, biosensors, cytotoxicity test samples, and other fields that are currently limited by conventional methods of manufacture. The present invention provides methods and apparatus which integrate computer-aided design; Boolean, scaling, mirroring, smoothing, and/or other modifying operations; Magnetic Resonance Imaging (MRI)/Computed Tomography (CT) and other patient specific data import capabilities; heterogeneous material and multi-part assembly capabilities; biomimetic and non-biomimetic design capabilities; multiple types of nozzles capable of handling a wide range of materials as well as multiple modes of nozzle operation such as droplet deposition, extrusion, and spraying; and/or a biologically friendly design capable of direct cell deposition, to create a very powerful and versatile manufacturing process. Further, these methods and apparatus provide for simultaneous deposition of cells with scaffolding materials to form cell-seeded tissue substitutes. Accordingly, the methods and apparatus of the present invention permit construction of complex or smart tissue scaffolds capable of eliciting complex behaviors of cells including, but not limited, to growth, migration, differentiation, and expression. Tissue engineering scaffolds produced in accordance with the methods and/or using the devices of the present invention can also assist with the flow and transport of vital nutrients and oxygen, and the removal of waste products required by cells seeded within the scaffolds.

BACKGROUND OF THE INVENTION

Most tissue engineering techniques basically consist of seeding a tissue scaffold or culture dish with cells that are grown in an incubator. The scaffold fabrication and the cell seeding are two separate processes. These techniques are very limited in their level of sophistication. The scaffolds tend to be simple structures made out of a single material, with some post-processing techniques in the slightly more complicated scaffolds. Organized, heterogeneous cellular structures are very difficult to create, and impossible to create at the complexity level of an organ using standard techniques. Seeding these kinds of scaffolds may not be enough to stimulate the cells into responding in the desired manner. A complex scaffold is required to elicit complex behavior from a cell. A new generation of tissue scaffolds is required to take the next step in tissue engineering which essentially moves away from simple scaffolds toward complex scaffolds. A cell is a very sophisticated machine with programming built into its genetic code. A complex scaffold takes advantage of this built-in programming through the incorporation of various biological factors that direct cell growth, migration, differentiation, and expression. In addition, constructs can be created that could help with the flow and transport of vital nutrients and oxygen, and the removal of waste products.

Layered manufacturing has been suggested as being well suited to the field of biology. This has resulted in much research being conducted within the field of computer-aided tissue engineering (CATE). Unfortunately, many Solid Freeform Fabrication (SFF) techniques are not biologically friendly using techniques that cannot handle a wide range of wet materials, gels or solutions. Also, many SFF techniques utilize harsh solvents, high temperatures, high pressures, and other factors that are not conducive to biological systems. Many SFF techniques, such as stereolithography, fused deposition methods, and powder/binder-based techniques, are capable of creating tissue scaffolds, but cannot directly deposit cells or biological factors into the scaffold. This has resulted in the creation of different techniques to handle direct cell deposition.

Weiss, et al. have described a method for building bone tissue scaffolds using SFF (Reischmann et al. *Electrotechnik and Informationstechnik* 2002 7/8:248-252; Weiss et al. *Journal of Manufacturing Systems* 1997 16(4): 239-248). This process consists of taking a CAD model of a three-dimensional structure of a bone implant, slicing the model into layers, taking laminated sheets of scaffold material, seeding the layers with cells or growth factors, and stacking them on top of each other. This process was designed for the purpose of constructing bone implants, not to provide a flexible process of creating various types of organs or biologically/chemically integrated systems and thus has several disadvantages with respect to construction of tissue engineering devices. For example, the method is limited in materials since soft, gel-like materials cannot be used as scaffold layers. This is a problem since many biological parts are soft or wet. Also, each layer of the scaffold is made with one type of sheet material. Thus, it is difficult to have two or more different materials within the same layer level. Accuracy and recalibration is an issue as well since the scaffold layers are moved from station to station. Thus, although a simple scaffold can be created by this method, a complex scaffold with controlled concentration gradients is difficult, if not impossible, to create. This is a serious disadvantage since cells are very responsive to even the slightest differences in concentration gradients.

Yan and Xiong, et al. have disclosed the concept of using layered manufacturing methods and multi-nozzle deposition extrusion and jetting processes (Xiong et al. *Scripta Materialia* 2002 46:771-776; Yan et al. *Materials Letters* 2003 57:2623-2628). Their process includes spraying and deposition of heterogeneous materials with different material properties. However, full CAD integration is not described. Nor is there any description of the ability to import an assembly of multiple STL files for printing a complex, heterogeneous, three-dimensional structure. This is a vital design component when building complex parts such as biomimetic parts where MRI or CT data is incorporated into the final design, or integrating both biomimetic parts and non-biomimetic parts into a novel scaffold design.

A SFF method using a syringe-based system to dispense liquids, which is well suited for working with biological materials such as cells and hydrogels has also been described (Landers et al. *Macromol Mater Eng* 2000 282:

17-21; Landers et al. *Kunststoffe/plast Europe* 2001 91(12): 21-23; Landers et al. *Biomaterials* 2002 23: 4437-4447). The primary focus of this method is the building of scaffolds and seeding the scaffold. The deposition system used is a single nozzle device that requires cartridge swapping to change materials. This is not a very practical system for depositing multiple, heterogeneous materials such as different types of cells and growth factors all within the same scaffold layer. Further, it is difficult to take a multiple part assembly of STL files and print out a complex, biologically designed scaffold utilizing this method. Thus, there are limitations in this method with respect to the CAD integration aspect as well.

A syringe-based system for the extrusion of hybrid polymer materials embedded with glass using layered SFF manufacturing has also been described (Calvert et al. *Materials Science and Engineering* 1998 C6:167-174). This system also uses a single nozzle and does not incorporate CAD, thus being limited to simple designs written in Microsoft Qbasic. This system is not capable of creating heterogeneous designs within a single layer. Thus, this system is sufficient for creating basic scaffolds, but falls short of being able to create intricate scaffolds containing both biomimetic and non-biomimetic features.

A microsyringe deposition system has also been described (Vozzi et al. *Materials Science and Engineering* 2002 C20: 43-47; Vozzi et al. *Biomaterials* 2003 24: 2533-2540). This system utilizes a single-nozzle deposition system which has fine resolution, but is limited because of the glass capillary used for deposition. The glass capillary limits the range of viscosities that are usable due to pressure limits, and also limits the types of solutions and suspensions that can be deposited due to clogging. The device is envisaged for integration with CAD, but whether their working device could actually utilize STL files is unclear. Also, the single nozzle system makes multi-material, heterogeneous deposition difficult.

A single-nozzle, automated extrusion system that can utilize basic STL files has been described as well (Ang et al. *Materials Science and Engineering* 2002; C20:35-42). It is unclear whether this system can be utilized to produce multi-part, heterogeneous STL files. This single nozzle process also makes constructing complex parts very difficult, and limits the diverse range of materials available for deposition.

Mironov, et al. discuss the basic principles of organ printing, which involves direct deposition of cells using a multi-nozzle printing system (Mironov et al. TRENDS in Biotechnology 2003 21(4):157-161). A general basic concept of organ printing involving CAD in the preprocessing stage incorporating either patient specific MRI/CT data or artificial computer generated biomimetic constructs is set forth. However, there is no mention of the value of CAD beyond simply imitating biology. In addition, there are serious limitations with their disclosed multi-nozzle system which uses the same type of syringe thus limiting the types of materials that can be deposited. In order to build good 3-dimensional structures, relatively viscous solutions are required, which means high pressure. High pressure, however, may not be compatible with cells. High pressure systems handling viscous materials have the problem of not being able to deposit fine structures with fine concentration gradients. Finally, there is a flaw in the process described in this reference because they do not consider the fact that CAD programs do not have heterogeneous material capabilities. Thus, they neglect a non-trivial and difficult step by assuming that they can create a multi-material part in CAD and print it out using multiple nozzles, which is not necessarily the case.

U.S. Pat. No. 6,139,574 (Vacanti, et al. Oct. 31, 2000) discloses vascularized tissue regeneration matrices formed by SFF techniques. Use of CAD and SFF techniques for the creation of tissue scaffolds is mentioned. Further, they mention the possibility of using multiple printheads and different kinds of SFF techniques. However, there is no description of direct cell deposition. The reason for this is that the method described is not biologically friendly to cells. Thus, the described method requires depositing the scaffold material and bioactive materials first to create the scaffold, and then seeding the cells externally relying upon cell migration to populate the scaffold. Further, the inkjet printing method described by Vacanti creates problems for cellular deposition unless significant steps are taken to protect cells from shear stresses that would tear the cell apart.

U.S. Pat. No. 6,143,293 (Weiss, et al. Nov. 7, 2000) discloses assembled scaffolds for three dimensional cell culturing and tissue generation. The method used is primarily oriented towards building hard, bone-type scaffold structures and creation of soft, gel-like scaffolds using this method may be difficult. Further heterogeneous capabilities are limited to materials that can be added on top of the layer, but not within the layer itself. The method of Weiss et al. also utilizes prefabricated layers thus necessitating an assembly stage, which then requires extra steps to calibrate, align, and affix the layers. Means for affixing the layers such as barbs, or other mechanical affixing means is a disadvantage that may result in later complications due to wear, bone remodeling, or incompatibilities in material properties. The method described by Weiss et al. thus lacks versatility and flexibility.

U.S. Pat. No. 6,027,744 and U.S. Pat. No. 6,171,610 (Vacanti, et al. Feb. 22, 2000 and Vacanti, et al. Jan. 9, 2001) describe guided development and support of hydrogel-cell compositions. Methods described therein use hydrogel-cell compositions as a means of tissue scaffold construction and rely upon injecting the hydrogel-cell material into the tissue scaffold. The described method does not include layered fabrication methods or CAD. Direct deposition of cells into a scaffold while constructing the scaffold is also not mentioned.

U.S. Pat. No. 6,176,874 (Vacanti, et al. Jan. 23, 2001) discloses vascularized tissue regeneration matrices formed by SFF fabrication techniques. Again, the described method does not include layered fabrication methods or CAD nor direct deposition of cells into a scaffold while constructing the scaffold.

U.S. Pat. No. 6,454,811 (Sherwood, et al. Sep. 24, 2002) discloses composites for tissue regeneration and methods of manufacture thereof. This method primarily focuses on three-dimensional printing (3DP) for tissue engineering. Although there is mention that other methods of SFF could be used, no explicit details are provided. Further, there is no mention of CAD integration, heterogeneous materials, multi-part assemblies, and multi-nozzle printing within a CAD environment. In addition, the majority of the SFF methods described are not biologically friendly for direct cell deposition. For example, stereolithography, selective laser sintering, and fused deposition modeling cannot directly deposit cells due to heating and toxicity issues which will kill cells. Ballistic particle manufacturing also has problems due to shear stresses that can damage cells, which are very sensitive and require low pressure or a protective method to reduce the shear stresses experienced by the cell. The described 3DP method is also unable to directly seed cells into the interior of the part that is being constructed. This process also requires post-processing in which powder, which functions both as the part and the support material, has to be removed after finishing the printing process. Thus, while this method can be used to create porous structures, the pores are filled with powder during the printing stage. It is only after printing has been completed that the powder is removed to open up the pores. Thus, cells cannot be directly printed at specific locations inside the part. Instead, cells must migrate from the outside of the scaffold, into the interior of the scaffold. This is a serious disadvantage when trying to create reproducibility between histotypic or organ culture samples. Finer features require additional post-processing, such as salt-leaching, which again makes direct cellular deposition impossible.

U.S. Pat. No. 6,547,994 (Monkhouse, et al. Apr. 15, 2003) describes a process for rapid prototyping and manufacturing of primarily drug delivery systems with multiple gradients, primarily involving a 3DP technique. These 3DP techniques share the same shortcomings as described for U.S. Pat. No. 6,454,811.

U.S. Pat. No. 6,623,687 (Gervasi, et al. Sep. 23, 2003) describes a process for producing three-dimensional objects by constructing an interlaced lattice construct using SFF to create a functional gradient material. There is brief mention of the possibility of using this technique to create tissue engineered constructs such as veins and arteries. However, there is no demonstration of use in this application.

SUMMARY OF THE INVENTION

An aspect of the present invention is related to a method for production of complex components or parts and devices used, for example, as tissue scaffolds and constructs. The method of the present invention integrates computer-aided design; Boolean, scaling, mirroring, smoothing, and/or other modifying operations; MRI/CT and other patient specific data import capabilities; heterogeneous material and multi-part assembly capabilities; biomimetic and non-biomimetic design capabilities; multiple types of nozzles capable of handling a wide range of materials; multiple modes of nozzle operation such as droplet deposition, extrusion, and spraying; and/or a biologically friendly design capable of direct cell deposition. Components and devices produced in accordance with the method of the present invention are useful, for example, in tissue engineering, organ/cell printing, tissue scaffolds, tissue cultures, biochips, biosensors, and cytotoxicity test samples Another aspect of the present invention is related to an apparatus or system for production of devices requiring the integration of different biological elements such as an artificial organ and/or devices requiring integration of biological and artificial elements. The apparatus comprises a multi-nozzle biopolymer deposition system capable of extruding biopolymer solutions and living cells for freeform construction of three-dimensional tissue scaffolds. The apparatus can, simultaneously with the scaffold construction, deposit controlled amount of cells, growth factors, or other bioactive compounds with precise spatial position to form well-defined cell-seeded tissue constructs. The apparatus or system also enables the fabrication of larger or thicker tissue constructs with complex layouts, such as vascular networks.

BRIEF DESCRIPTION OF THE FIGURES

FIGS. 4a through 4d show the creation of a triple-layered scaffold produced in accordance with the same techniques as set forth in FIG. 4a through 4c. FIG. 4a shows the initial CAD model, followed by creation of porous outer layer (FIG. 4b), and subsequent creation of a compact middle layer (FIG. 4c).

FIGS. 5a through 5c show creation of an exemplary replacement scaffold in accordance with the present invention wherein CAD-MRI/CT and Boolean operations are combined to introduce a pre-designed structural feature into the replacement scaffold. In this example, a vascular tree was created in CAD that followed a basic pathway analogous to artery-arteriole-capillary-venule-vein (FIG. 5a). Using scaling and Boolean operations a portion of an implant was quickly "vascularized" (FIG. 5b-c). CATE to was used to create channels in an implant. FIG. 5a shows the vascular tree created in CAD.

FIG. 6a through 6d shows creation of a tissue scaffold designed with built-in functional components that are non-biological in nature. In this example, a drug chamber was designed in CAD (FIG. 6a). This feature was then added to the scaffold.

FIG. 7a through 7c shows various three-dimensional hydrogel scaffolds produced with the methods and apparatus of the present invention.

As shown in FIG. 9, a variety of materials were simultaneously deposited, containing different alginate solutions at concentrations in the range of 0.1%-0.4% (w/v), with the lighter gray material (indicated by A) also containing an alginate microspheres suspension and a darker gray (indicated by B) chitosan hydrogel.

DETAILED DESCRIPTION OF THE INVENTION

There is a vital demand for improving tissue engineering techniques. Organ transplantation and the need for donors is a problem within this country. With increasing life expectancy and a growing aging population, the need for organ transplantation is ever greater. However, there is currently no process capable of creating seeded tissue scaffolds for implantation with the complexity of organs.

In addition to organ transplantation, there is a need for improved methods of cytotoxicity testing for the pharmaceutical, cosmetics, and food industries. This would help resolve the ethical problem of animal testing, and in a more practical sense, also help reduce cost as well. Creating sophisticated, three-dimensional organ cultures could replace simple two-dimensional cultures that are not necessarily reliable in determining cytotoxicity. In addition, organ culture, organotypic cultures, and histotypic cultures are not easily standardizable. By having an automated manufacturing process for creating artificial organ cultures, there would be standardization, and the ability to compare experimental results between different organ cultures.

In addition to the need for organs and better methods of cytotoxicity testing, there are also the developing areas of biochips, bioelectronics, biosensors, bionics, cybernetics, artificial organs, and bioactive tissue scaffolds. These devices require the integration of both biological and artificial elements. Any device that could improve this integration would be a significant advance to those fields.

The present invention provides methods and systems for producing devices that can satisfy the above described need.

Figure 1:
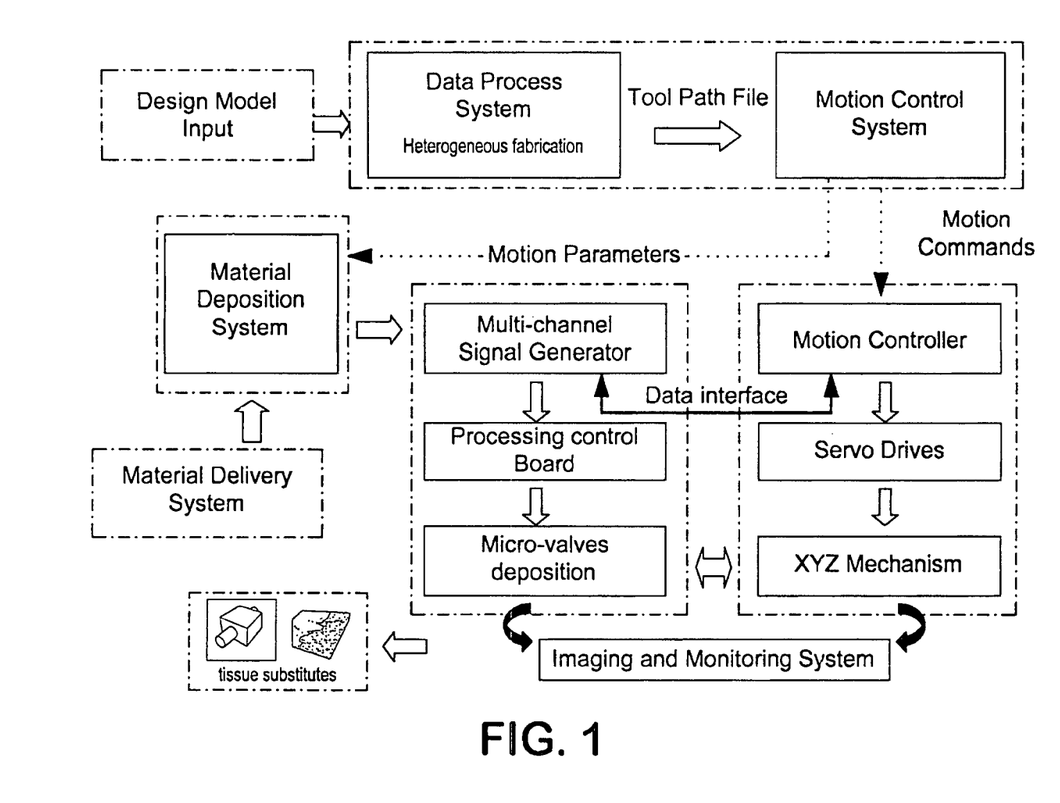
FIG. 1 provides a flow diagram of a system configuration of a multi-nozzle biopolymer deposition apparatus of the present invention.

FIG. 1 shows a flow diagram of a system configuration of a multi-nozzle biopolymer deposition apparatus of the present invention.

As shown in FIG. 1, in the methods and apparatus of the present invention, a data processing system processes a designed scaffold model and converts it into a layered process tool path.

The apparatus further comprises a motion control system driven by this layered manufacturing technique.

The material delivery system for the apparatus comprises multiple nozzles of different types and sizes, thus enabling the deposition of specified hydrogels with different viscosities for constructing three-dimensional tissue scaffolds. In a preferred embodiment, four types of nozzles are used in the system or apparatus. Examples include, but are not limited to, solenoid-actuated nozzles, piezoelectric glass capillary nozzles, pneumatic syringe nozzles, and spray nozzles, with size ranges varying from about 30 µm to about 500 µm. The system can continuously extrude hydrogels, or form hydrogels in single droplets with picoliter volumes. The multiple nozzle capability allows for simultaneous deposition of cells, growth factors, and scaffold materials, thus enabling the construction of heterogeneous scaffolds with bioactive compounds, or establishing functional gradient scaffolds with different mechanical/structural properties in different scaffold regions.

Figure 2:
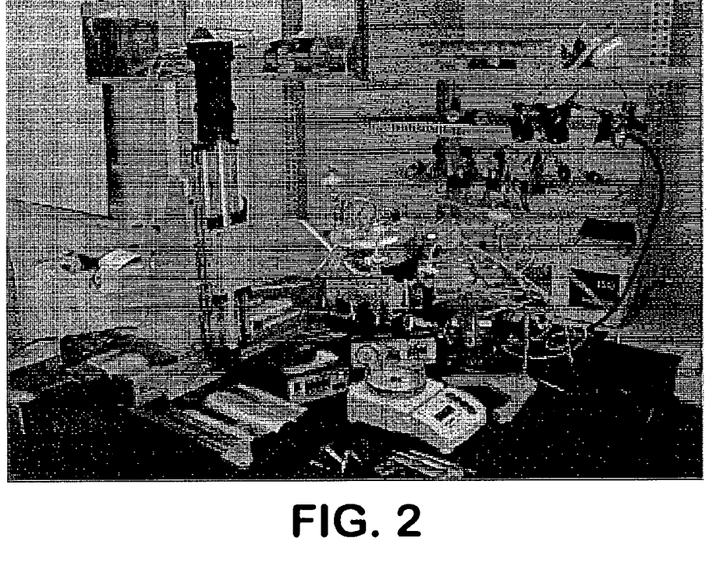
FIG. 2 provides a photograph of an exemplary multi-nozzle biopolymer deposition apparatus of the present invention.

FIG. 2 provides a photograph an exemplary multi-nozzle biopolymer deposition apparatus of the present invention.

Step one of the methods and apparatus of the present invention comprise integrated computer-aided design capabilities. The methods and system of the present invention may further comprise as step two MRI/CT and other patient specific data import capabilities thereby allowing adaptation of each manufactured part for each person's unique geometry.

CAD provides the user with the basic ability to create both biomimetic and non-biomimetic designs and features. These can be created by the deposition of electrically conductive materials, magnetic materials, thermally conductive materials, mechanically active materials, bioactive elements, genetic materials and vectors, and so forth.

Figure 3A:
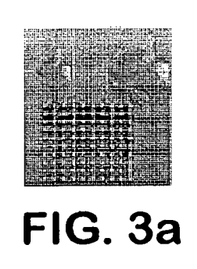
FIGS. 3a through 3c show the creation of a multi-layered scaffold in accordance with the present invention to design a porous channel structure as a CAD model (FIG. 3a), and use of patient specific MRI/CT data to design the required anatomical replacement scaffold model (FIG. 3b), and further use of Boolean operation to produce a porous, interconnected replacement scaffold as the finished implant (FIG. 3c).
Figure 3B:
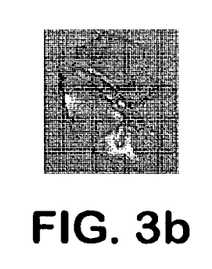
Figure 3C:
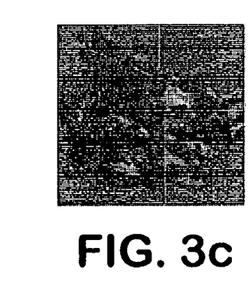
Figure 4A:
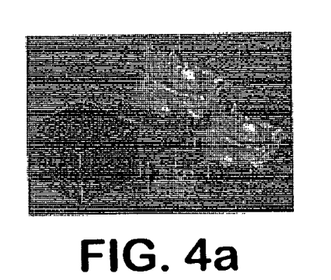
Figure 4B:
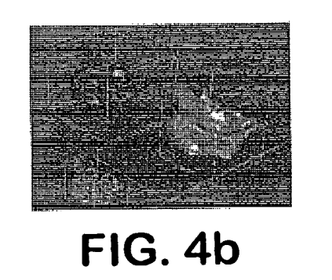
Figure 4C:
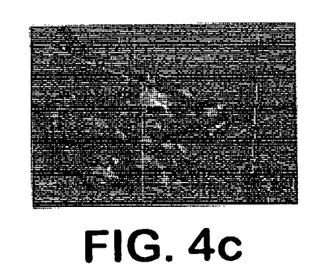
Figure 4D:
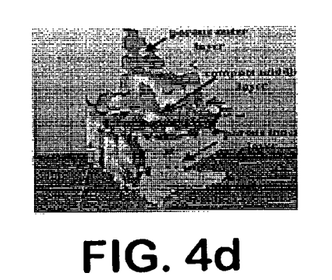
FIG. 4d shows a cutaway view of the finished triple layer implant with porous inner layer.

For example, as shown in FIG. 3a through 3c, CAD can be used to design a porous channel structure as a CAD model (FIG. 3a). Patient specific MRI/CT data is then used to design the required anatomical replacement scaffold model (FIG. 3b). Boolean operation is then used to produce a porous, interconnected replacement scaffold (FIG. 3c).

As shown in FIG. 4a through 4d, using these same simple methodologies of the present invention, a triple-layered structure with a porous outer layer, a compact middle layer, and a porous inner layer is created.

Figure 5A:
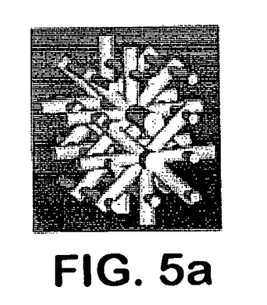
Figure 5B:
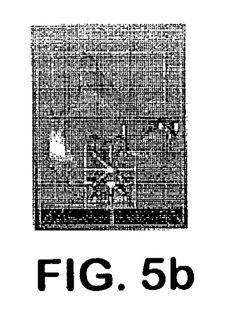
As shown in FIG. 5b, the CAD design was imported and rescaled as STL files in Geomagic (a reverse engineering software).
Figure 5C:
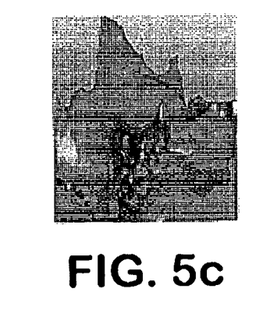
FIG. 5c shows the scaffold structure after Boolean operation.

Further, as shown in FIG. 5a through 5c, CAD-MRI/CT and Boolean operations can be combined in accordance with the present invention to introduce a pre-designed structure feature into a scaffold such as replacement scaffold. For example, as shown in FIG. 5, a vascular tree can be created in CAD that follows a basic pathway analogous to artery-arteriole-capillary-venule-vein (FIG. 5a). Using scaling and Boolean operations a portion of an implant can then be quickly "vascularized".

Figure 6A:
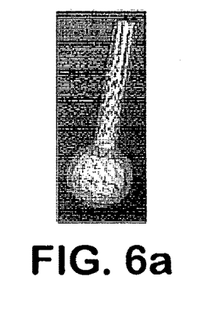
Figure 6B:
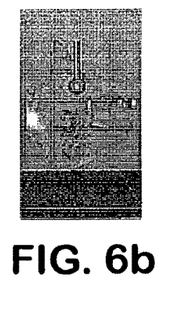
FIG. 6b shows the scaffold before subtraction of the chamber insert from the scaffold and FIG. 6c shows the scaffold following chamber insertion. An existing vascular tree design was also incorporated into the scaffold as shown in the cutaway of FIG. 6d, which depicts both the chamber and channels of this integrated delivery system.
Figure 6C:
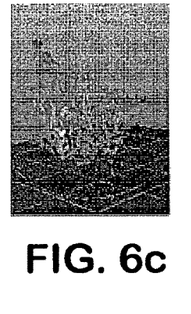
Figure 6D:
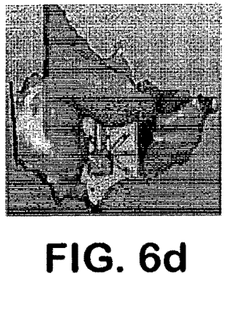

With power of the computer-aided tissue engineering, tissue scaffolds can be designed with built-in functional components that are non-biological in nature. For example, growth factors and drugs play vital roles in tissue engineering. Accordingly, a drug chamber for storage and delivery of such agents can be designed in CAD (FIG. 6a) and then added as a feature to the scaffold (FIG. 6b-d). As shown in FIG. 6d, an existing vascular tree design was also incorporated into the scaffold. Other non-biomimetic features such as inlet and outlet ports and attachment interfaces can be added in similar fashion thus allowing for quick assembly of sophisticated scaffolds using the methods and apparatus of the present invention.

As shown by these exemplary scaffold embodiments of FIGS. 3 through 6, following CAD design, the methods and the apparatus of the present invention may further comprise Boolean, scaling, smoothing, mirroring, and/or other modifying operations which can be used to design and incorporate biomimetic and non-biomimetic features. Thus, step two of the method of the present invention may comprise use of Boolean, scaling, smoothing, mirroring, and/or other operations to modify the design. A combination of these types of operations adds great versatility to the design process. Examples of Boolean operations are addition and subtraction operations used to create voids or parts that fill voids, conforming to their geometry and anatomical shape. Boolean additive and subtractive capabilities also allows the operator to create a set of standardized or "stock" parts and features that can be reused and recycled in multiple designs. While such operations can be skipped when creating relatively simple devices, when building complex devices, use of one or more of these operations are extremely useful and expand the design capabilities immensely.

The ability to create both biomimetic and non-biomimetic features permits one of skill in the art to produce a device such as a scaffold comprising, for example, electrically conductive materials, magnetic materials, thermally conductive materials and mechanically active materials as well as bioactive elements, genetic materials and vectors. Examples of non-biomimetic features which can be incorporated into devices produced by this method and apparatus include, but are not limited to, electrically conductive material deposited, extruded, laid down, in order to create wires, circuits, biochips, etc., mechanically active elements such as microvalves or miniature pumps and actuators built or incorporated into the finished part to create a microfluidic device, biochip, biosensor, a specialized component or prefabricated element, such as an integrated circuit, valve, or piezoelectric element added through an automated device that is designed to place it into the part being constructed, a tip or other device used to direct electrical stimulation or to apply a charge to direct ion flow, stimulate muscle contraction, cause changes to the cell nucleus, and a tip or device with a voltage potential between the tip and substrate in order to deposit material onto the substrate via a process similar to electrospinning.

The methods and apparatus of the present invention may further comprise multi-nozzle capability thus permitting deposit of multiple materials within the same layer. Different types of specialized nozzles provide versatility to the process of the present invention to handle a wide range of materials such as suspensions, gels, and a wide range of viscosities ranging from water to viscous glues. Further, multiple modes of nozzle operation can be provided including, but not limited to, droplet deposition, extrusion, and spraying operations, thereby allowing control of different levels of resolution and material properties. For example, fine microdroplet deposition may be used for adding minute concentrations of biological factors, and extrusion may be used to create a strong scaffold structure.

Accordingly, in step three of the method and apparatus of the present invention, interface software is used to convert the CAD designed device of step 1 or steps 1 and 2 into a heterogeneous material and multi-part assembly model that can be used for multi-nozzle printing. This is an important step of the method as it allows the user to take a multi-material CAD design and print it out using multiple nozzles.

The methods and apparatus of the present invention may further comprise heterogeneous material and multi-part assembly capabilities so that in step four of the method of the present invention the design is printed out using the different, specialized nozzles. This step also vastly increases the repertoire of materials that are usable, and thus expands the type of designs that can be built, ranging for example from biological to non-biological scaffolds, parts, devices, etc. The nozzles are also capable of handling multiple modes of nozzle operation such as droplet deposition, extrusion, and spraying, thus allowing for control of different levels of resolution and material properties. A very important ability of the process of the present invention is direct seeding of a part without having to rely upon cellular ingrowth or migration to reach the interior of the part due to the precision deposition of the seeding materials.

Figure 7A:
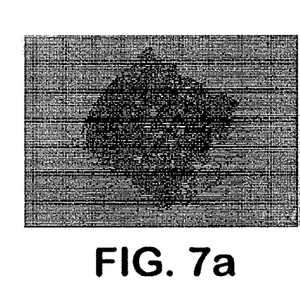
FIGS. 7a and b show a three-dimensional hydrogel scaffold comprising 10 layers of calcium alginate, extruded as a 3% (w/v) alginate filament within a cross-linking solution (FIG. 7a) and simple alginate geometrical pattern (FIG. 7b). By varying the size of the syringe nozzle, the pressures used, and the type of deposition method (extrusion), alginate filaments within the 30-40 micron range (FIG. 7c) for 3% (w/v) sodium alginate solution with a 5% (w/v) calcium chloride cross-linking solution, at 0.50 psi were produced.
Figure 7B:
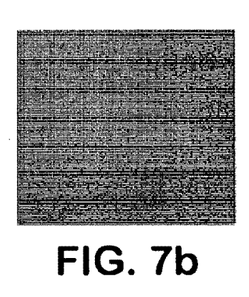
Figure 7C:
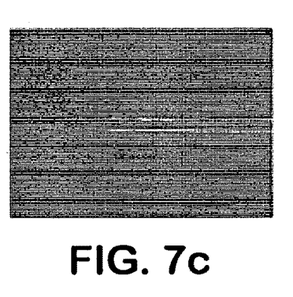
Figure 8:
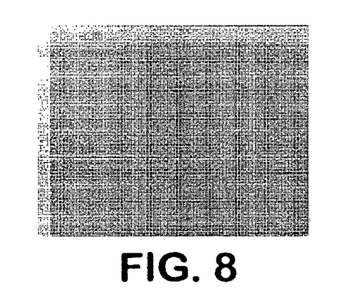
FIG. 8 shows results of a cell deposition/extrusion study conducted using a hydrogel produced with the apparatus and method of the present invention. For these experiments, the hydrogel was produced from alginate hydrogel mixed with human endothelial cells at a cell concentration 750,000 cells/ml with sodium alginate: 1.5% (w/v), nozzle: EFD 200 μm at pressure: 2 psi, deposition speed: 10 mm/s, and calcium chloride: 5% (w/v).
Figure 9:
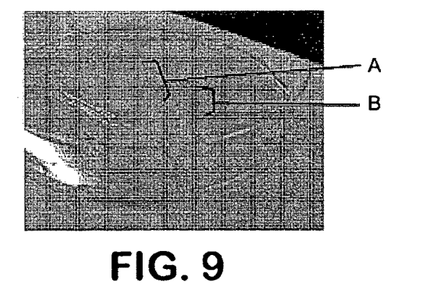
FIG. 9 shows a hydrogel from similar experiments to those depicted in FIG. 8 wherein multi-nozzle heterogeneous deposition of different materials was used to produce the hydrogel.

Exemplary hydrogels depicting versatility achieved through use of the apparatus and methods of the present invention are depicted in FIGS. 7 through 9.

As can be seen, using the method and system of the present invention a complex, multi-material CAD design can be printed out using multiple nozzles. This is a significant advantage of the methods and system of the present invention that cannot be accomplished using CAD and solid modeling programs incapable of modeling heterogeneous parts with different material properties.

The methods and system of the present invention utilize biologically friendly design capabilities so that cells and/or biological factors can be deposited directly within and/or onto the scaffold.

Direct cell deposition is a very important capability that is often overlooked, and is a significant difference from prior method. Many have not considered and have failed to see its importance in creating organ cultures with reproducible samples. Being able to create organ, organotypic, or histotypic cultures by using the exact same assembly procedures with reliability will revolutionize the pharmacological, food, and cosmetics testing industries. Organ cultures will be a much more reliable indicator of true drug behavior in vivo than current cytotoxicity testing methods. This will reduce greatly the cost of drug testing and manufacturing thereby lowering the cost of medication and health care costs. It will also reduce the amount of animal testing that is done as well. Organ cultures that can be compared with each other can provide insight into other fields as well such as molecular and cell biology, genetics, and tissue engineering.

In addition, direct cell deposition creates tissue structures that are more histologically accurate. That is, cells are placed next to other cells that they are normally next to within an in vivo environment. They can also be deposited in their proper location and ratios. This has huge significance, since cells do not exist alone, but rather, rely upon each other for proper function and maintenance. Cell-cell signaling and communication either from direct contact or paracrine signaling is vital for proper cellular behavior, differentiation, and proliferation. Also, the extracellular matrix produced by cells is vital for cellular function.

CAD integration capabilities of the methods and system of the present invention allow for the incorporation of non-biological elements into the design including, but not limited to, drug chambers, access ports, biotelemetry for doctors and biosensors. These non-biomimetic features can be created in CAD, as shown for example in FIG. 6, saved as a part, and then reused over and over, being incorporated into many different designs. Thus, integration of CAD in the process of the present invention enables not just the building of devices that imitate nature, but also the building of devices that can assist or go beyond nature.

The multi-nozzle system with different types of nozzles used in the methods and system of the present invention permits layering of multiple components into the device. Nozzles could be different in sizes, diameters, tip types, or in different operational mechanisms, such as solenoid, piezoelectric, and pneumatic air-regulated nozzles. For example, one nozzle can be specialized for cell deposition, while another nozzle can be optimized for depositing viscous structural members.

As shown in FIG. 1, implementation of the method and apparatus of system of the present invention involves use of a automatic control system, including a computer with software for CAD and medical imaging process ability to perform Boolean operations, mirroring, smoothing and three-dimensional reconstruction from MRI/CT to tissue replacement model; a XYZ positioning system inclusive of motion controllers and motors with an XYZ axis; a multi-nozzle system preferably comprising at least a microdroplet/fine resolution nozzle and a high viscosity/extrusion nozzle, as well as nozzle controllers, fluid reservoirs, and filters; and a pressure system inclusive of pressure tanks, pressure chambers, compressor/vacuum pumps, pressure sensors, and regulators.

In addition to the above-preferred embodiment, alternative variations of the methods and system are possible.

In one embodiment, a device can be constructed by either moving the platform that the device is being constructed on, or by moving the print head, or by a combination of both through controlling the XYZ positioning system.

Alternative nozzles or other devices can also be used to provide various coating or washings. For example, biochemical surface treatment can be performed via a nozzle or other device, for example, by washing, spraying, etc., simultaneously with the deposition of scaffolding materials through other nozzle(s). A coating material can also be sprayed on the device simultaneously with the deposition of the scaffolding material through other nozzle(s), or a coating material can be sprayed onto a single layer or layers of the device. An additional nozzle or other device can also be used to add a support material or temporary scaffolding that can later be removed from the finished part, for example, a reversible gel, simultaneously with the deposition of the scaffolding material through other nozzle(s). An additional nozzle can also be used to deposit drops-on-demand drugs, or lines of powder or solid materials, simultaneously with the deposition of the scaffolding material through other nozzle(s). An additional nozzle can also be used to deliver energy to speed the scaffold solidification, for example, to transmit a UV or Laser through an optical fiber simultaneously with the deposition of the scaffolding material through other nozzle(s). An additional nozzle can also be used to deposit, extrude or pattern electrically conductive materials within the scaffold simultaneously with the deposition of the scaffolding material through other nozzle(s) to generate wired, circuited, or biochip embedded scaffolds. An additional nozzle can also be used to transmit/deposit fluid simultaneously with the deposition of the scaffolding material through other nozzle(s). The fluid can be applied to the part for various purposes such as cooling, sterilization, cross-linking, solidification, etc. When using fluids, the part can be created in a container capable of holding fluids (a dish, a culture plate well, a fluid tank, etc.). The fluid level can be incremented by the same height as the layer being formed, thus raising the fluid level, or, the height level of the part could be decremented, thus lowering it into the fluid.

In-situ sterilization can be incorporated into the method of the present invention as well and can be done in several ways. In one embodiment, a solution with antibiotics such as penicillin is added through the multi-nozzle deposition system while making the device or afterwards. In another embodiment, a sterilizing solution (non-antibiotic) is added to one of the nozzles for deposition or post-sterilization. An alternative device to a nozzle, as part of the multi-nozzle deposition system, can also be used such as device emitting ultraviolet radiation, heat, or gamma irradiation.

The method and system of the present invention may further comprise imaging capabilities such as an ultrasonic transducer that can be used for imaging the device while it is being built. Alternatively, an optical imaging apparatus, such as a microscope, can be used to provide visual information, or provide data for feedback in a closed-loop control system. An optical imaging apparatus can also be used to monitor fluorescence and reporter gene activities which can be used for cell counting, calculating the presence of proteins, DNA expression, metabolic activity, cell migration, etc. Atomic force microscopy and scanning tunneling microscopy, can also provide information about the device at nanoscale resolution.

Sensing devices can also be incorporated into the methods and system to provide relevant data such as temperature, or to monitor chemical reactions, chemicals released during production, and/or mechanical forces such as shear during production. Such sensing devices can be used to create a feedback control mechanism to regulate the process parameters in an automated fashion.

Mechanical agitation or stimulation devices such as ultrasonic, subsonic; and/or sonic transducers can also be incorporated into the methods and system to stimulate the device mechanically during construction. The stimulations will help to improve the device structural properties, for example, homogeneity of the cell and scaffolding material distribution.

Further, mechanical devices can be used to stamp, press, adjust, move, cut, and trim the device during construction.

Thus, the methods and system of the present invention comprise multiple steps and elements that, when combined, create a very powerful and robust method and system for manufacturing devices within the biological field, as well as other fields outside of biology. For example, devices produced in accordance with the methods and system described can be used as reproducible organ cultures. Such organ cultures are expected to be very useful in cytotoxicity testing (i.e. food, drug, and cosmetics industry), and other fields such as the study of tissue engineering, molecular biology, and cell biology. The greatly improved reproducibility between samples of organ cultures is achieved using the method and system of the present invention by directly depositing cells and biological factors while building the device. If one relies upon inward cell migration into the completed tissue scaffold or construct, there is no consistency in the location, distribution, or ratios of the cells. With the automated methods and system of the present invention, reproducibility between heterogeneous, 3-dimensional organ cultures is achieved. The cells, biological factors, and scaffold materials can be precisely deposited in the same locations, in the same manner, and with the same concentrations. This results in organ cultures that are assembled in the exact same manner, and so can be used to make comparisons between different organ culture test samples. In addition, direct cell deposition using the methods and system of the present invention permits creation of tissue engineering devices that are more natural histologically. Cells can be placed next to other cells in a spatial pattern and orientation similar to their in vivo environment. They can also be deposited in their proper ratios, thus resulting in a much better tissue scaffold than produced currently.

Additional ramifications of the methods and system of the present invention include scaling up and mass production. The introduction of computer-aided design and automated assembly allows for mass production of tissue samples, cultures, and organs, that can be used for pharmacological testing, for example, in testing hundreds of variations of cancer-fighting drugs. Automation can lead to not only increased design complexity, but also increased speed, consistency, and quality control.

The following nonlimiting examples are provided to further illustrate the present invention.

Examples

The apparatus depicted in FIG. 2 was used to construct various three-dimensional biopolymer based tissue scaffolds.

For example, shown in FIG. 7 are, several three-dimensional hydrogel scaffolds (10 layers, calcium alginate), extruded as a 3% (w/v) alginate filament within a cross-linking solution (FIG. 3a) and simple alginate geometrical pattern (FIG. 3b). Depending upon the size of the syringe nozzle, the pressures used, and the type of deposition method (extrusion), alginate filaments within the 30-40 micron range (FIG. 3c) were created for 3% (w/v) sodium alginate solution with a 5% (w/v) calcium chloride cross-linking solution, at 0.50 psi.

Further, cell deposition/extrusion studies were conducted by extruding alginate hydrogel mixed with human endothelial cells at a cell concentration: 750,000 cells/ml with sodium alginate: 1.5% (w/v), nozzle: EFD 200 µm at pressure: 2 psi, deposition speed: 10 mm/s, and calcium chloride: 5% (w/v) (see FIG. 4). Experiments were also preformed testing multi-nozzle heterogeneous deposition of different materials. As shown in FIG. 5, a variety of materials were simultaneously deposited, containing different alginate solutions at concentrations in the range of 0.1%-0.4% (w/v), with the light gray material designated by A also containing an alginate microspheres suspension and a darker gray chitosan hydrogel designated as B.

The invention claimed is:

1. A method for multi-nozzle biopolymer deposition of heterogeneous materials to create or modify a composite biopolymer multi-part three-dimensional assembly having at least one biomimetic and at least one non-biomimetic feature, the method comprising:
    (a) utilizing a CAD environment to design and/or modify a composite multi-part assembly, thereby producing a CAD design;
    (b) converting the CAD design into a three-dimensional heterogeneous material and multi-part assembly model in a format suitable for three-dimensional, multi-nozzle printing, wherein the design comprises at least one biomimetic feature and at least one non-biomimetic feature; and
    (c) printing the composite assembly by simultaneously depositing the heterogeneous materials using multiple, different, specialized nozzles, wherein the simultaneous depositing includes direct deposition of cells and biological factors.

2. The method of claim 1, wherein the utilizing step includes performing at least one Boolean operation.

3. The method of claim 1, wherein the utilizing step includes performing at least one scaling operation.

4. The method of claim 1, wherein the utilizing step includes performing at least one smoothing operation.

5. The method of claim 1, wherein the utilizing step includes performing at least one mirroring operation.

6. The process of claim 1, wherein the composite biopolymer multi-part three-dimensional assembly is one or more selected from the group consisting of: a tissue engineering device, an artificial organ, a tissue scaffold, an artificial vasculature or channel system, and a cytotoxicity testing sample.

7. The process of claim 1, wherein the composite biopolymer multi-part three-dimensional assembly is a biochip.

8. The process of claim 1, wherein the composite biopolymer multi-part three-dimensional assembly is a biosensor.

9. The process of claim 1, wherein the composite biopolymer multi-part three-dimensional assembly is a scaffold selected from the group consisting of: a bionic scaffold, a cybernetic scaffold, a mechanoactive, and a bioactive tissue scaffold.

10. The method of claim 1, wherein the printing step includes:
    controlling an ultraviolet-radiation-emitting nozzle to deliver ultraviolet energy to speed solidification of the one or more deposited heterogeneous materials.

* * * * *